United States Patent
Tateyama et al.

(10) Patent No.: US 9,719,123 B2
(45) Date of Patent: Aug. 1, 2017

(54) URINE SAMPLE ANALYZER AND URINE SAMPLE ANALYZING METHOD

(71) Applicant: SYSMEX CORPORATION, Kobe-shi, Hyogo (JP)

(72) Inventors: Shota Tateyama, Kobe (JP); Masanori Kawano, Kobe (JP); Masatsugu Ozasa, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 214 days.

(21) Appl. No.: 14/524,211

(22) Filed: Oct. 27, 2014

(65) Prior Publication Data
US 2015/0118706 A1  Apr. 30, 2015

(30) Foreign Application Priority Data
Oct. 29, 2013 (JP) .................. 2013-224552

(51) Int. Cl.
*G01N 33/00* (2006.01)
*C12Q 1/04* (2006.01)
(Continued)

(52) U.S. Cl.
CPC .............. *C12Q 1/04* (2013.01); *G01N 15/14* (2013.01); *G01N 15/1436* (2013.01);
(Continued)

(58) Field of Classification Search
None
See application file for complete search history.

(56) References Cited

U.S. PATENT DOCUMENTS 6,165,740 A * 12/2000 Fukuda ................ C12Q 1/04
435/283.1
7,632,683 B2 * 12/2009 Kawashima ..... G01N 33/56961
422/73
(Continued)

FOREIGN PATENT DOCUMENTS

JP   H08-170960 A   7/1996
JP   H11-023446 A   1/1999
(Continued)

OTHER PUBLICATIONS

"LIVE/DEAD FungaLight (TM) Yeast Viability Kit MP 34952", Molecular Probes Product Information, Jan. 1, 2005, pp. 20-2005, XP055168356, Retrieved on Feb. 9, 2015 from https://tools.lifetechnologies.com/content/sfs/manuals/mp34952.pdf.

*Primary Examiner* — Jill Warden
*Assistant Examiner* — Brittany Fisher
(74) *Attorney, Agent, or Firm* — Mots Law, PLLC

(57) ABSTRACT

Disclosed is a urine sample analyzer for analyzing particles contained in a urine sample and outputting analytical results. The analyzer includes a flow cell that accepts a measurement specimen, the measurement specimen comprising a urine sample mixed with a reagent, a light irradiation unit positioned to irradiate the flowing measurement specimen with light, a light detector that detects light from individual particles in the flowing measurement specimen, and a data processor that receives signal from the light detector, processes the signal to obtain parameter information corresponding to a length of a cell cluster, and classifies fungi in the measurement specimen into groups by using the parameter information.

19 Claims, 15 Drawing Sheets

(51) Int. Cl.
*G01N 33/493* (2006.01)
*G01N 15/14* (2006.01)
*G01N 15/10* (2006.01)

(52) U.S. Cl.
CPC ..... *G01N 15/1459* (2013.01); *G01N 15/1463* (2013.01); *G01N 33/493* (2013.01); *G01N 2015/1006* (2013.01); *G01N 2015/1402* (2013.01); *G01N 2015/1493* (2013.01); *G01N 2015/1497* (2013.01)

(56) References Cited

U.S. PATENT DOCUMENTS

| | | | | |
|---|---|---|---|---|
| 2007/0013906 | A1* | 1/2007 | Kawate | G01N 15/1012 356/243.2 |
| 2010/0047856 | A1* | 2/2010 | Takata | C12Q 1/04 435/39 |
| 2012/0225475 | A1* | 9/2012 | Wagner | G01N 15/14 435/288.7 |
| 2013/0177950 | A1* | 7/2013 | Osada | C07D 493/10 435/118 |

FOREIGN PATENT DOCUMENTS

| | | |
|---|---|---|
| JP | 2001-149091 A | 6/2001 |
| JP | 2005-102644 A | 4/2005 |
| JP | 2006-105625 A | 4/2006 |
| JP | 2007-255954 A | 10/2007 |
| JP | 1857805 A2 | 11/2007 |

\* cited by examiner

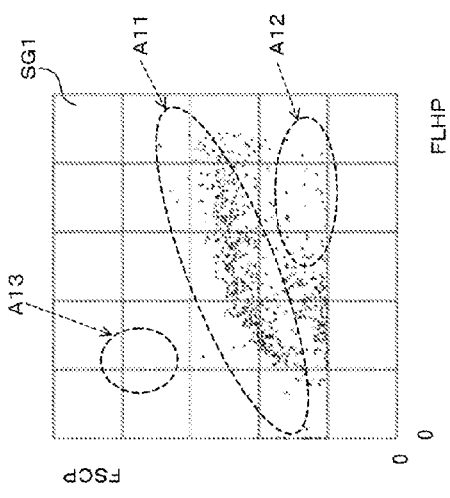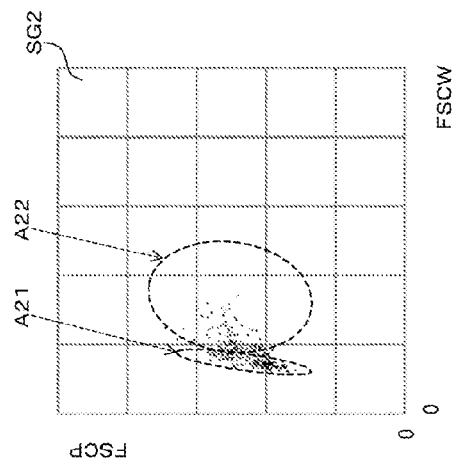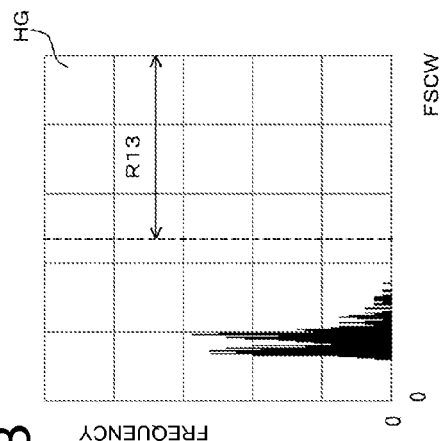
FIG. 8A
FIG. 8B
FIG. 8C

URINE SAMPLE ANALYZER AND URINE SAMPLE ANALYZING METHOD

CROSS REFERENCE TO RELATED APPLICATIONS

This application claims priority from prior Japanese Patent Applications No. 2013-224552, filed on Oct. 29, 2013, entitled "URINE SAMPLE ANALYZER AND URINE SAMPLE ANALYZING METHOD", the entire contents of which are incorporated herein by reference.

FIELD OF THE INVENTION

The invention relates to a urine sample analyzer and a urine sample analyzing method for analyzing urine particles, and more particularly to a urine sample analyzer and a urine sample analyzing method for use in analysis of fungi.

BACKGROUND

Urine particles contained in urine are analyzed in order to determine an abnormal part in a kidney or a urinary tract or its cause. For example, a urinary tract infection is often caused by a bacterial infection but may be caused by fungi. For this reason, urine analysis includes detection of fungi, as well as detection of bacteria.

For example, Japanese Patent Application Publication No. 2006-105625 (Patent Literature 1) and Japanese Patent Application Publication No. 2007-255954 (Patent Literature 2) disclose a method of analyzing urine particles by flow cytometry. In this method, a urine sample is subjected to a staining process, and a distribution diagram is generated based on a scattered light signal and a fluorescence signal obtained from each particle component. Then, discrimination is made between yeast-like fungi and other particles, based on a difference between distribution areas on the distribution diagram.

Fungi, although collectively so called, have various forms, and some fungi are budding; others are not budding. The budding fungi include fungi in which divided cells form a cluster, and hypha-like budding fungi. The above Patent Literatures 1, 2 do not disclose how to classify fungi according to different forms of fungi. However, if fungi can be subclassified according to the forms and then be presented as test results, the information thus obtained can be used for diagnosis and medical treatment.

SUMMARY OF THE INVENTION

The scope of the invention is defined by the appended claims, and not by any statements within this summary.

An embodiment relates to a urine sample analyzer for analyzing particles contained in a urine sample and outputting analytical results. The embodiment comprises a flow cell that accepts a measurement specimen, the measurement specimen comprising a urine sample mixed with a reagent, a light irradiation unit positioned to irradiate the flowing measurement specimen with light, a light detector that detects light from individual particles in the flowing measurement specimen, and a data processor that receives signal from the light detector, processes the signal to obtain parameter information corresponding to a length of a cell cluster, and classifies fungi in the measurement specimen into groups by using the parameter information.

Another embodiment relates to a urine sample analyzer for analyzing particles contained in a urine sample and outputting analytical results. The embodiment comprises a flow cell that accepts a measurement specimen, the measurement specimen comprising a urine sample mixed with a reagent, a light irradiation unit positioned to irradiate the flowing measurement specimen with light, a light detector configured to detect light from individual particles in the flowing measurement specimen, and a data processor that receives signal from the light detector and processes the signal to determine first parameter information corresponding to a length of a cell cluster and second parameter information corresponding to number of cells in the cell cluster, wherein the data processor classifies fungi in the measurement specimen into at least budding fungi and non-budding fungi by using the first parameter information and the second parameter information.

A further embodiment relates to a urine sample analyzing method. The embodiment comprises preparing a specimen by mixing a urine sample with a reagent, flowing the prepared specimen through a flow cell, irradiating the specimen flowing through the flow cell with light, detecting light from individual particles contained in the flowing measurement specimen to generate a detection signal, generating parameter information from the detection signal, the parameter information corresponding to a length of a cell cluster, and classifying fungi in the measurement specimen into groups having different forms by using the parameter information.

BRIEF DESCRIPTION OF DRAWINGS

FIGS. 8A to 8C are graphs illustrating a scattergram and a histogram according to Operational Example 1.

EMBODIMENTS

The following embodiment is the invention as applied to a urine sample analyzer for analyzing particles such as blood cells, fungi, bacteria, casts, and epithelial cells contained in a urine sample. The urine samples as measurement objects include urine sampled from a living body, such as raw urine, urine in a ureter, urine in a bladder, and urine in a urethra, as well as discharged urine.

Figure 1:
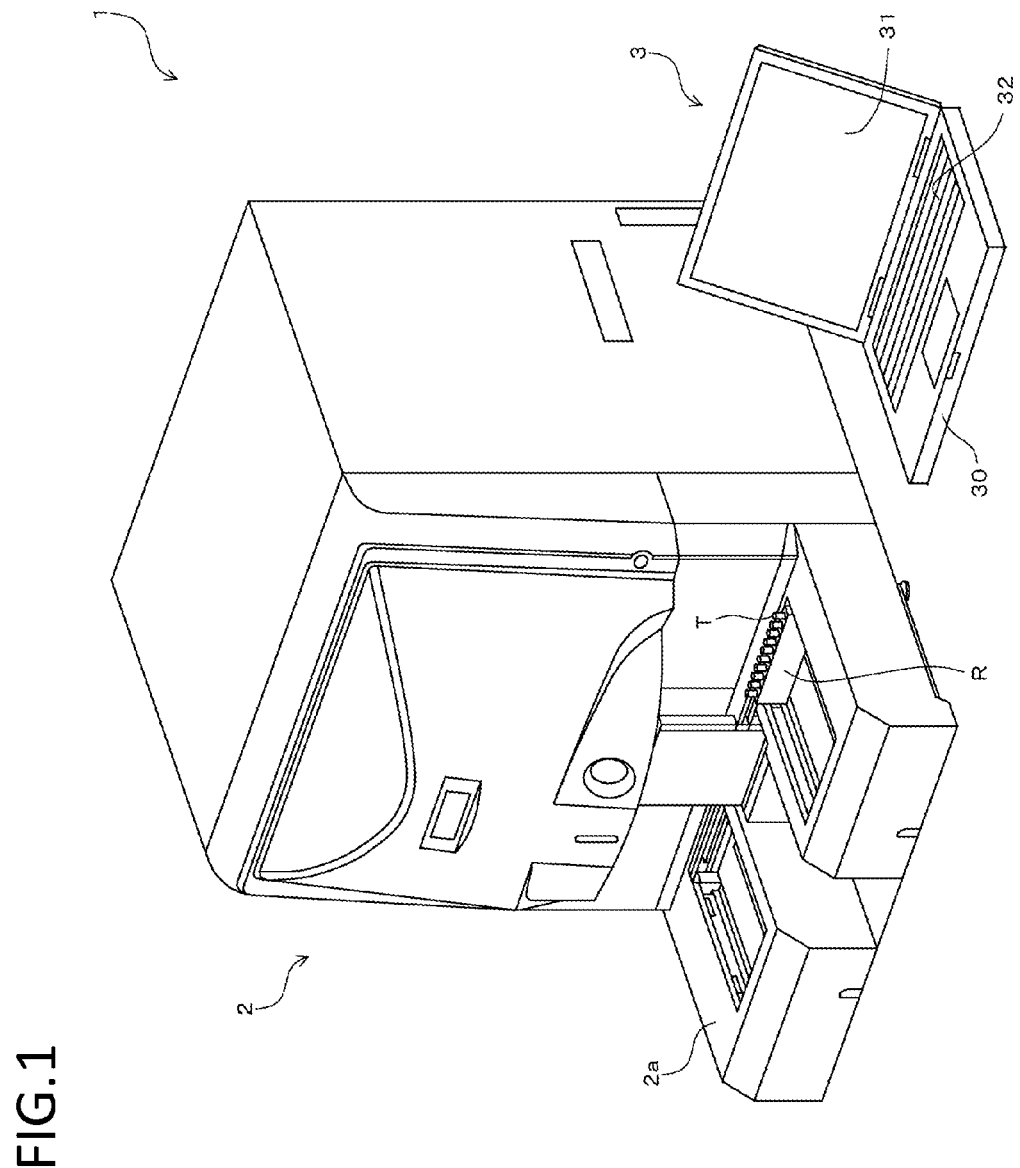
FIG. 1 is an illustration of a configuration of an external appearance of a urine sample analyzer according to an embodiment.

The embodiment is described below with reference to the drawings. FIG. 1 is an illustration of a configuration of an external appearance of urine sample analyzer 1. Urine sample analyzer 1 includes measuring device 2 which optically measures particles contained in a urine sample by a flow cytometer, and information processing apparatus 3 which processes measured data (to be described later) outputted by measuring device 2. Measuring device 2 is provided at its front with transport unit 2a, and transport unit 2a transports rack R holding plural containers T accommodating urine samples. Information processing apparatus 3 includes main body 30, display unit 31 that displays analytical results or the like, and input unit 32 that receives a command from an operator.

Figure 2:
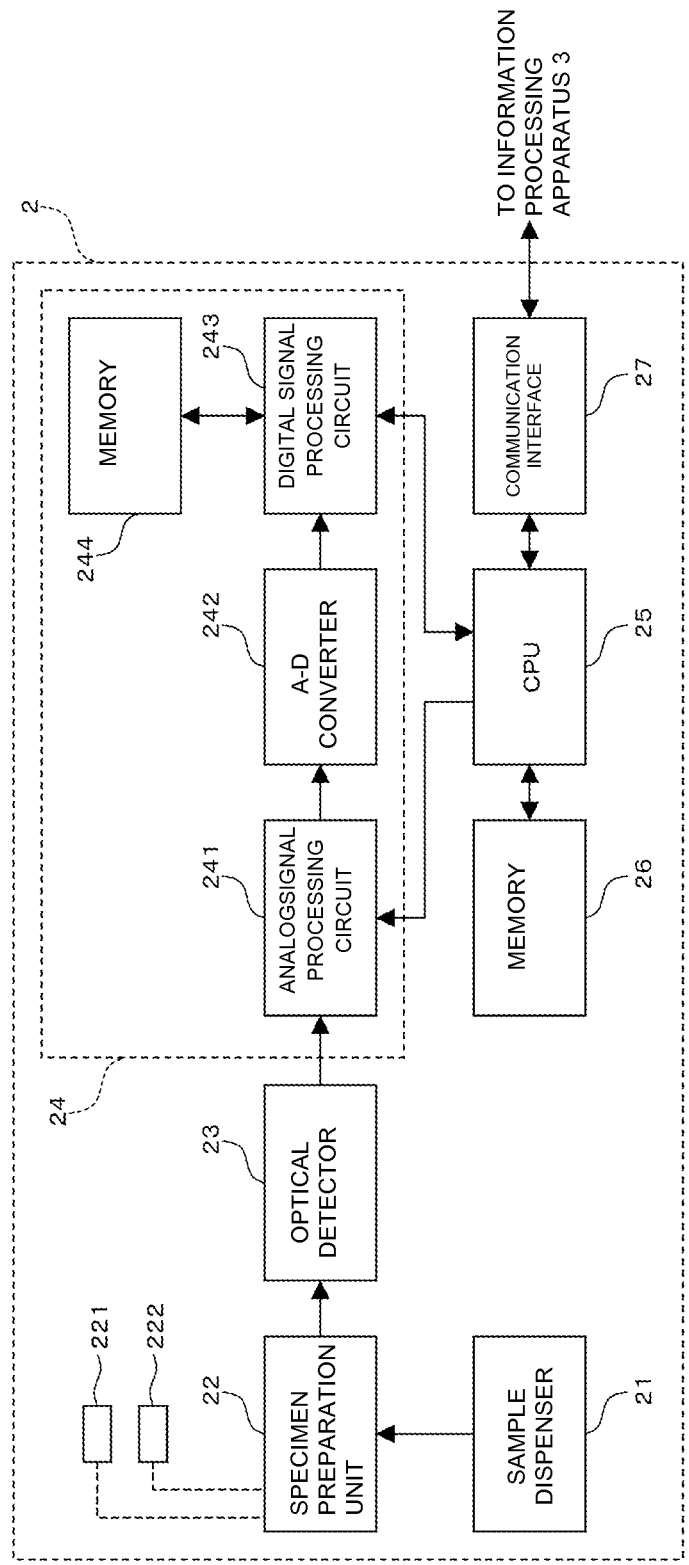
FIG. 2 is a block diagram illustrating a configuration of a measuring device according to the embodiment.

FIG. 2 is a block diagram illustrating a configuration of measuring device 2.

Measuring device 2 includes sample dispenser 21, specimen preparation unit 22, optical detector 23, signal processing circuit 24, CPU (central processing unit) 25, memory 26, and communication interface 27. Signal processing circuit 24 includes analog signal processing circuit 241, A-D (analog-to-digital) converter 242, digital signal processing circuit 243, and memory 244.

Sample dispenser 21 sucks a predetermined amount of urine sample from each of containers T transported by transport unit 2a and feeds the predetermined amount of urine sample to specimen preparation unit 22. Specimen preparation unit 22 includes a mixing chamber and a pump (not illustrated). Also, containers 221, 222 are connected via tubes to specimen preparation unit 22. Container 221 accommodates a reagent for staining a nucleic acid. The reagent contains dye for staining the nucleic acid, and cyanine base dye, for example, is preferably used. Container 222 accommodates a diluent, and the diluent contains a reagent, which causes damage to a cell membrane to proceed with the passage of the reagent in container 221 through the membrane and acts to hemolyze red blood cells. In a case of measurement of cells having nucleic acids such as fungi or white blood cells, in the mixing chamber, the reagents and the diluent fed from containers 221, 222 are mixed with a sample fed from sample dispenser 21 thereby to prepare a measurement specimen. The measurement specimen prepared in the mixing chamber is fed through the pump to flow cell 205 (see FIG. 3) of optical detector 23, together with a sheath liquid. In a case of measurement of particles having no nucleic acid such as red blood cells, a reagent and a diluent accommodated in an unillustrated container are mixed with a sample thereby to prepare a measurement specimen.

Figure 3:
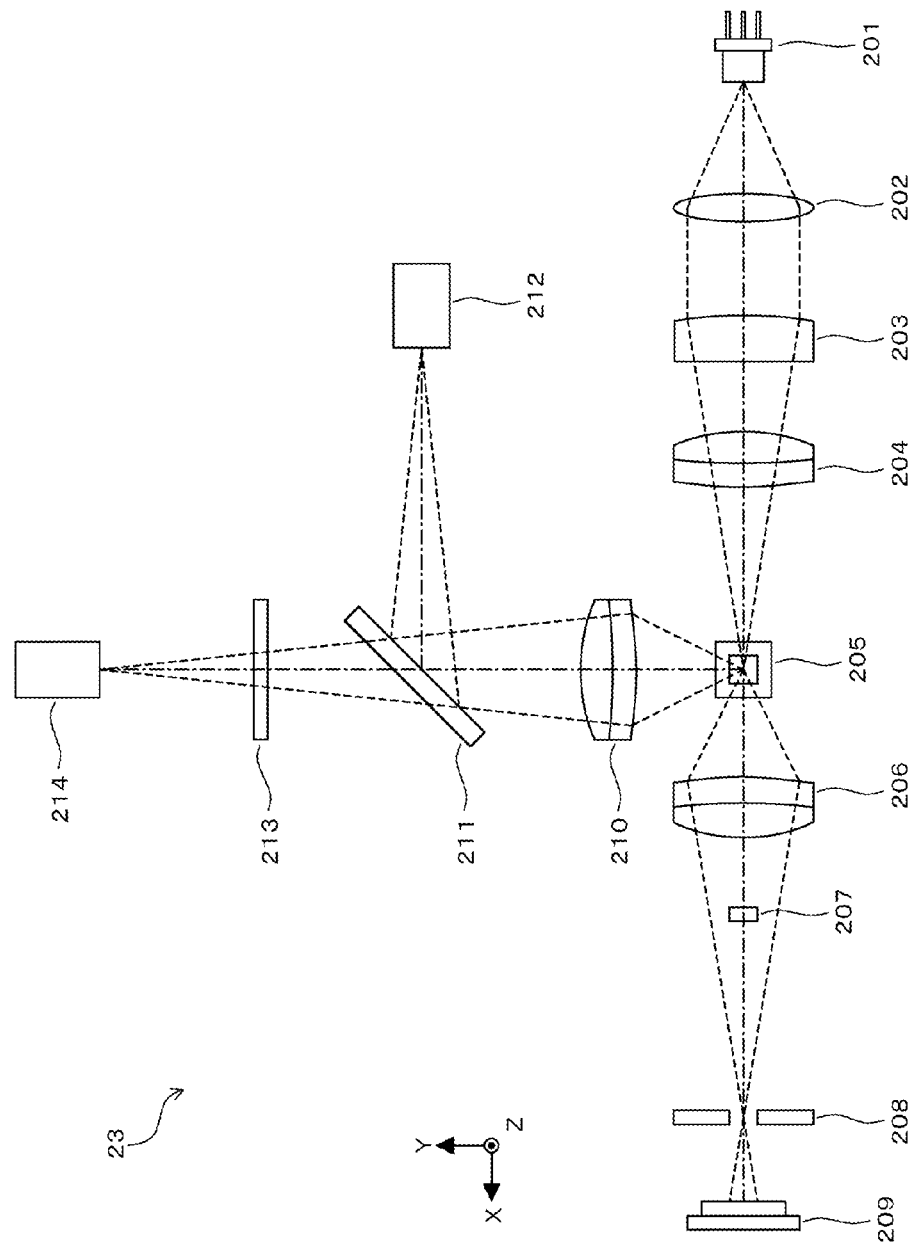
FIG. 3 is a schematic representation illustrating a configuration of an optical detector according to the embodiment.

FIG. 3 is a schematic representation illustrating a configuration of optical detector 23.

Optical detector 23 includes semiconductor laser light source 201, collimator lens 202, cylindrical lens 203, condenser lens 204, flow cell 205, converging lens 206, beam stopper 207, pinhole 208, photodiode 209, converging lens 210, dichroic mirror 211, photomultiplier 212, spectroscopic filter 213, and photomultiplier 214.

Semiconductor laser light source 201 emits laser light having a wavelength of about 488 nm in a positive direction of an X axis. The laser light emitted by semiconductor laser light source 201 is collimated by collimator lens 202. The laser light having passed through collimator lens 202 is converged only in a Y axis direction by cylindrical lens 203. The laser light having passed through cylindrical lens 203 is focused in the Y axis direction and a Z axis direction by condenser lens 204. Thereby, a measurement specimen flowing through flow cell 205 in the Z axis direction is irradiated with the laser light emitted by semiconductor laser light source 201, in the form of a narrow beam long in the Y axis direction.

When particles in the measurement specimen are irradiated with the laser light, forward scattered light appears forward of flow cell 205 (or in the positive direction of the X axis) and side scattered light appears on a lateral side of flow cell 205 (or in a positive direction of the Y axis). Further, side fluorescence appears from nuclei of fungi, white blood cells or the like stained by the reagent in container 221, on the lateral side of flow cell 205 (or in the positive direction of the Y axis).

The forward scattered light is focused on the position of pinhole 208 by converging lens 206 arranged on the side of flow cell 205 in the positive direction of the X axis. Part of the light emitted by semiconductor laser light source 201, specifically, the laser light which has passed through flow cell 205 without being applied to the particles in the measurement specimen, is focused by converging lens 206 and is then cut off by beam stopper 207 so as not to enter photodiode 209. The forward scattered light, which has passed through pinhole 208 is detected by photodiode 209. Photodiode 209 outputs a forward scattered light signal (FSC) based on the detected forward scattered light.

The side scattered light is focused by converging lens 210 arranged on the side of flow cell 205 in the positive direction of the Y axis. The side scattered light, which has passed through converging lens 210 is reflected by dichroic mirror 211. The side scattered light reflected by dichroic mirror 211 is detected by photomultiplier 212. Photomultiplier 212 outputs a side scattered light signal (SSC) based on the detected side scattered light.

The side fluorescence is focused by converging lens 210, as is the case with the side scattered light. The side fluorescence that has passed through converging lens 210 passes through dichroic mirror 211, is passed through spectroscopic filter 213, and is detected by photomultiplier 214. Photomultiplier 214 outputs a side fluorescence signal (SFL) based on the detected side fluorescence.

Returning to FIG. 2, optical detector 23 outputs the forward scattered light signal (FSC), the side scattered light signal (SSC) and the side fluorescence signal (SFL) to analog signal processing circuit 241. Under a command from CPU 25, analog signal processing circuit 241 uses an amplifier to amplify the light-based electric signals outputted by optical detector 23, and outputs the amplified signals to A-D converter 242.

A-D converter 242 converts the electric signals outputted by analog signal processing circuit 241 into digital signals, and outputs the digital signals to digital signal processing circuit 243. Under a command from CPU 25, digital signal processing circuit 243 performs predetermined signal processing on the digital signals outputted by A-D converter 242. Thereby, signal waveforms corresponding to forward scattered light, side scattered light and side fluorescence that appear every time particles pass through flow cell 205 are obtained. In other words, the signal waveforms corresponding to the light rays are obtained according to particles (e.g. red blood cells, white blood cells, fungi, epithelial cells, casts, bacteria, and the like) contained in the measurement specimen. The obtained signal waveforms are stored in memory 244.

CPU 25 calculates plural feature parameters (e.g. a peak value, a width, and an area) corresponding to the forward scattered light, the side scattered light and the side fluorescence, from the signal waveforms stored in memory 244.

Figure 4A:
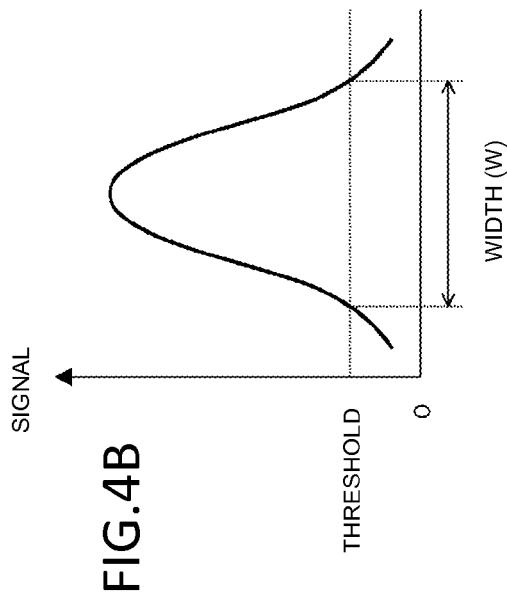
FIGS. 4A to 4C are graphs of assistance in explaining feature parameters according to the embodiment.
Figure 4B:
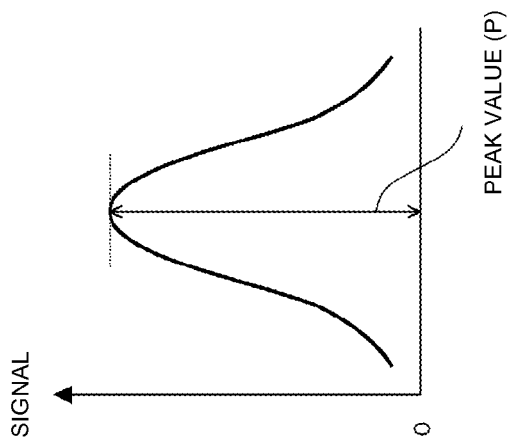
Figure 4C:
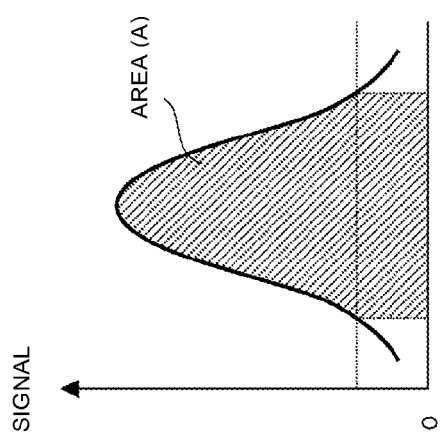

As illustrated in FIG. 4A, the peak value (P) is a maximum value of the signal waveform. As illustrated in FIG. 4B, the width (W) is a width of a portion of the signal waveform greater than a predetermined threshold. As illustrated in FIG. 4C, the area (A) is an area of a portion surrounded by the signal waveform and a line segment extending downward from a point of intersection of a predetermined threshold and the signal waveform. Incidentally, the thresholds for use in FIGS. 4B and 4C are set as appropriate for each feature parameter so that proper feature parameters can be obtained. The feature parameters of the light rays thus calculated are stored in memory 26.

CPU 25 transmits the calculated feature parameters (hereinafter called "measured data") of each particle to information processing apparatus 3 via communication interface 27. Also, CPU 25 receives a control signal from information processing apparatus 3 via communication interface 27, and drives parts of measuring device 2 under the control signal.

Figure 5:
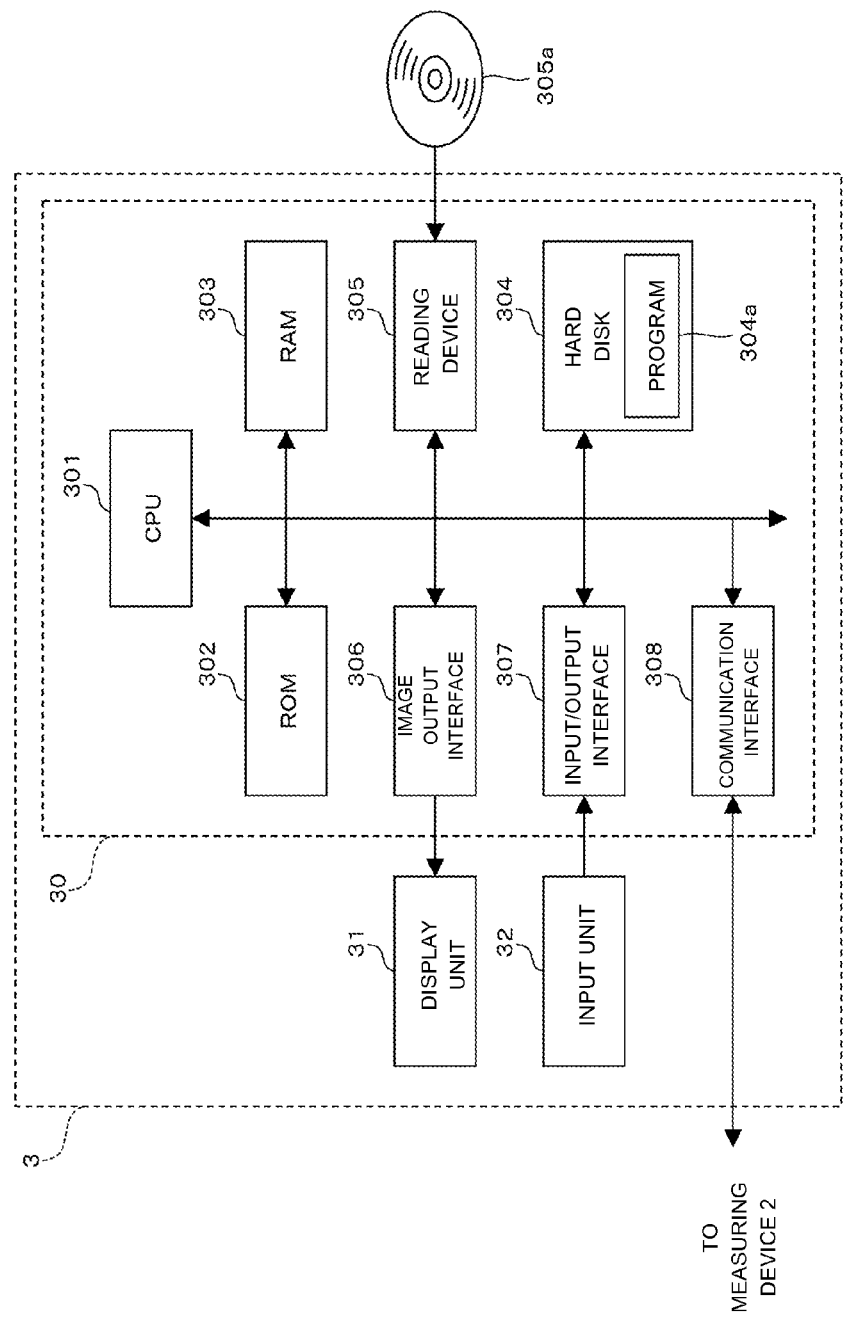
FIG. 5 is a block diagram illustrating a configuration of an information processing apparatus according to the embodiment.

FIG. 5 is a block diagram illustrating a configuration of information processing apparatus 3.

Information processing apparatus 3 is formed of a personal computer and is constructed of main body 30, display unit 31, and input unit 32. Main body 30 includes CPU 301, ROM (read only memory) 302, RAM (random access memory) 303, hard disk 304, reading device 305, image output interface 306, input/output interface 307, and communication interface 308.

CPU 301 executes a computer program stored in ROM 302 and a computer program loaded into RAM 303. RAM 303 is used to read out the computer programs stored in ROM 302 and hard disk 304. Also, for execution of the computer programs, RAM 303 is also utilized as a working area of CPU 301.

Hard disk 304 stores an operating system, the computer programs to be executed by CPU 301, and data for use in the execution of the computer programs. Also, hard disk 304 prestores program 304a for execution of an operation illustrated in FIG. 7, 10, 10C, 11A or 12A, and measured data received from measuring device 2 is stored in sequence. Reading device 305 is constructed of a CD drive, a DVD drive or the like, and can read out a computer program and data recorded on recording medium 305a. Incidentally, in a case where program 304a is recorded on recording medium 305a, program 304a read out from recording medium 305a by reading device 305 is stored in hard disk 304.

Image output interface 306 outputs a video signal according to image data to display unit 31, and display unit 31 displays an image based on the video signal. When the operator enters a command via input unit 32, input/output interface 307 accepts an input signal. Communication interface 308 is connected to measuring device 2, and CPU 301 transmits and receives a command signal and data to and from measuring device 2 via communication interface 308.

Description is given with regard to fungi as objects to be classified in the embodiment.

Figure 6A:
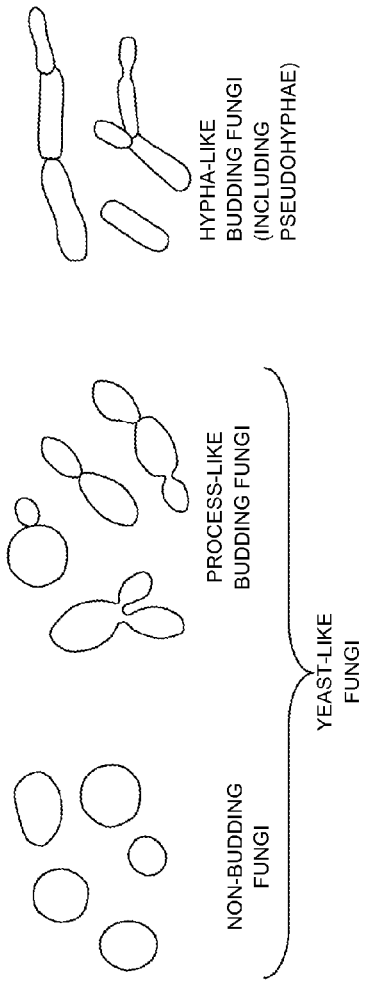
FIGS. 6A and 6B are a schematic representation illustrating forms of fungi according to the embodiment and a graph illustrating areas set in a scattergram, respectively.

Generally, fungi contained in a urine sample are classified into yeast-like fungi and hypha-like budding fungi, as illustrated in FIG. 6A. The yeast-like fungi are classified into non-budding fungi and process-like budding fungi. Pseudohyphae belong to a category of the hypha-like budding fungi. In the embodiment, the fungi contained in the urine sample are classified into the yeast-like fungi and the hypha-like budding fungi, and further, the yeast-like fungi are classified into the non-budding fungi and the process-like budding fungi.

The non-budding fungi are shorter than other fungi, and the process-like budding fungi are longer than the non-budding fungi. Also, the hypha-like budding fungi are still longer than other fungi. Therefore, in a case where the fungi are classified into the non-budding fungi, the process-like budding fungi, and the hypha-like budding fungi, parameters reflecting the lengths of the fungi can be used.

In a case where budding causes hyperplasia of fungi, first, a part of a mother cell projects and grows to form a daughter cell. Then, the daughter cell detaches from the mother cell to form a new mother cell. That is, plural cells are present with the mother cell before each daughter cell is detached therefrom, and only one cell is present in each newly produced daughter cell detached from the mother cell. Therefore, assuming that a fungus is regarded as a cluster of cells, the numbers of cells contained in the process-like budding fungus and the hypha-like budding fungus are larger than the number of cells contained in the non-budding fungus. Therefore, in a case where the fungi are classified into the non-budding fungi, the process-like budding fungi, and the hypha-like budding fungi, parameters reflecting the numbers of cells contained in the fungi can be used.

A width (FSCW) of the forward scattered light signal among the signals obtained by optical detector 23 illustrated in FIG. 3 reflects the length of a fungus which passes through flow cell 205. Therefore, the width (FSCW) of the forward scattered light signal can be used as a parameter to classify the fungi as described above. Also, a peak value (FSCP) of the forward scattered light signal among the signals obtained by optical detector 23 varies according to the surface area of a portion of the fungus irradiated with the beam, and thus reflects the number of cells contained in the fungus which passes through flow cell 205. In other words, as illustrated in the left and middle drawings of FIG. 6A, increases in the numbers of cells contained in the fungi cause increases in the surface areas of the fungi and thus tend to increase also the surface areas of the portions of the fungi irradiated with the beam. Therefore, the peak value (FSCP) of the forward scattered light signal is a parameter, which reflects the number of cells contained in the fungus. Therefore, the peak value (FSCP) of the forward scattered light signal can be used as a parameter to classify the fungi as described above.

Next, description is given with regard to an approach for classifying the fungi into the non-budding fungi, the process-like budding fungi, and the hypha-like budding fungi, by using the width (FSCW) and the peak value (FSCP) of the forward scattered light signal.

Figure 6B:
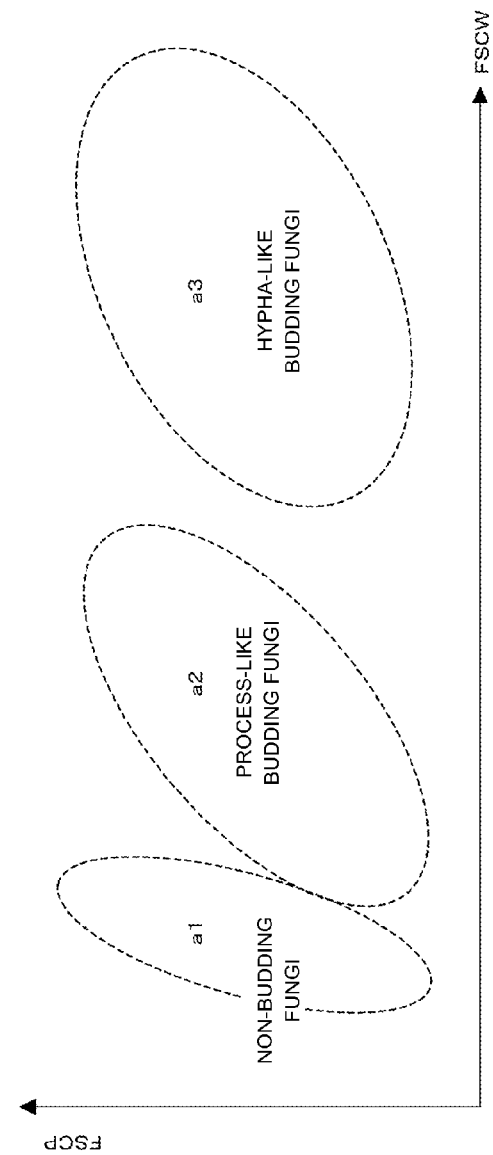

FIG. 6B is a graph illustrating in schematic form how forms of fungi are distributed on a scattergram having the width (FSCW) of the forward scattered light signal and the peak value (FSCP) of the forward scattered light signal as two axes, respectively. FIG. 6B illustrates in schematic form area a1 in which the non-budding fungi are distributed, area a2 in which the process-like budding fungi are distributed, and area a3 in which the hypha-like budding fungi are distributed. Particles contained in the areas (hereinafter, sometimes called "gates") are counted as the forms of fungi, respectively.

It is observed that the hypha-like budding fungi, the process-like budding fungi and the non-budding fungi are significantly different in the length of the cluster of cells. Preferably, therefore, areas a1 to a3 are set so that the forms of fungi can be classified mainly according to the difference in FSCW, on the scattergram having FSCW and FSCP as the two axes, respectively. Specifically, it is preferable that, as illustrated in FIG. 6B, area a1 in which the non-budding fungi are distributed, area a2 in which the process-like budding fungi are distributed and area a3 in which the hypha-like budding fungi are distributed be set so as to be arranged in sequence along the horizontal axis, as viewed from the side of the origin. Incidentally, the forms of fungi may be classified by using FSCW alone without using FSCP, taking only the length of the cluster of cells into account. For example, stepwise thresholds may be set for FSCW to classify the forms of fungi.

Note that the accuracy of classification is improved by optimizing the shapes or positions of the gates, based on a relationship between the positions of appearances and the forms of fungi in an empirically determined distribution map. Therefore, the setting of two-dimensional gates on the scattergram having two types of parameters as the axes, respectively, is preferable because of having a higher degree of freedom for optimization of the shapes or positions of the gates for purposes of good classification of the fungi, as compared to the setting of the thresholds for FSCW to classify the forms of fungi.

The shapes or positions of the gates are set by empirically determining the shapes and positions such that good discrimination of the forms of fungi is achieved, taking into account various conditions such as the compositions of the reagents, conditions of preparation of the measurement specimen, and photometry conditions.

FIG. 6B illustrates a preferable example of the positions and shapes of the gates. The hypha-like budding fungi are still longer than other fungi, and thus, it is preferable that area a3 be set at a position which is higher in FSCW than area a1 and area a2. Moreover, the fungi have various lengths, and thus, area a3 is set in a wider range than the other areas a1, a2. A difference in the length of cells between the non-budding fungi and the process-like budding fungi is less significantly observed than that from the hypha-like budding fungi, and thus, it is preferable that area a1 and area a2 be set at positions close to each other in a direction of the horizontal axis.

In the scattergram of FIG. 6B, each of areas a1 to a3 has a shape extending obliquely upward on the right. Even if the fungi belong to the same group in terms of form, a larger cell particle has a larger cell surface area (FSCP) and also has a larger length of the cell cluster (FSCW). Thus, the shape of the gate shown in FIG. 6B realizes that the groups of the forms of fungi are accurately determined.

For classification of the forms of fungi, classification into three groups, specifically, a group of non-budding fungi, a group of process-like budding fungi, and a group of hypha-like budding fungi, is preferable for the purpose of providing detailed test information; however, the number of groups classified may be set as appropriate according to the purpose. For example, the forms of fungi may be classified into two groups, specifically, a group of non-budding fungi and a group of process-like or hypha-like budding fungi, or may be classified into two groups, specifically, a group of yeast-like fungi and a group of hypha-like budding fungi.

As parameters for use in the classification of the forms of fungi, a parameter reflecting the length of the cells (for example, FSCW) may be used alone or in combination with a parameter reflecting the number of cells contained in the cell cluster (for example, FSCP). In particular, in a case of classification of the fungi into three groups of different forms, the classification may be made as illustrated by Operational Example 1 to be described later; specifically, giving attention to the fact that there is a significant difference in the length of the cell cluster, the yeast-like fungi and the hypha-like budding fungi are discriminated by using only a parameter reflecting the length of the cell cluster, and the yeast-like fungi are subclassified into the non-budding fungi and the process-like budding fungi by using the above-described two parameters in combination.

Description is given below with reference to FIGS. 7 to 12D with regard to five Operational Examples of urine sample analyzer 1 in a case of determination of the forms of fungi based on the above-described approach.

Operational Example 1

In Operational Example 1, fungi contained in a urine sample are classified into yeast-like fungi and hypha-like budding fungi by using FSCW alone, and the yeast-like fungi are subclassified into non-budding fungi and process-like budding fungi by using FSCW and FSCP.

Figure 7:
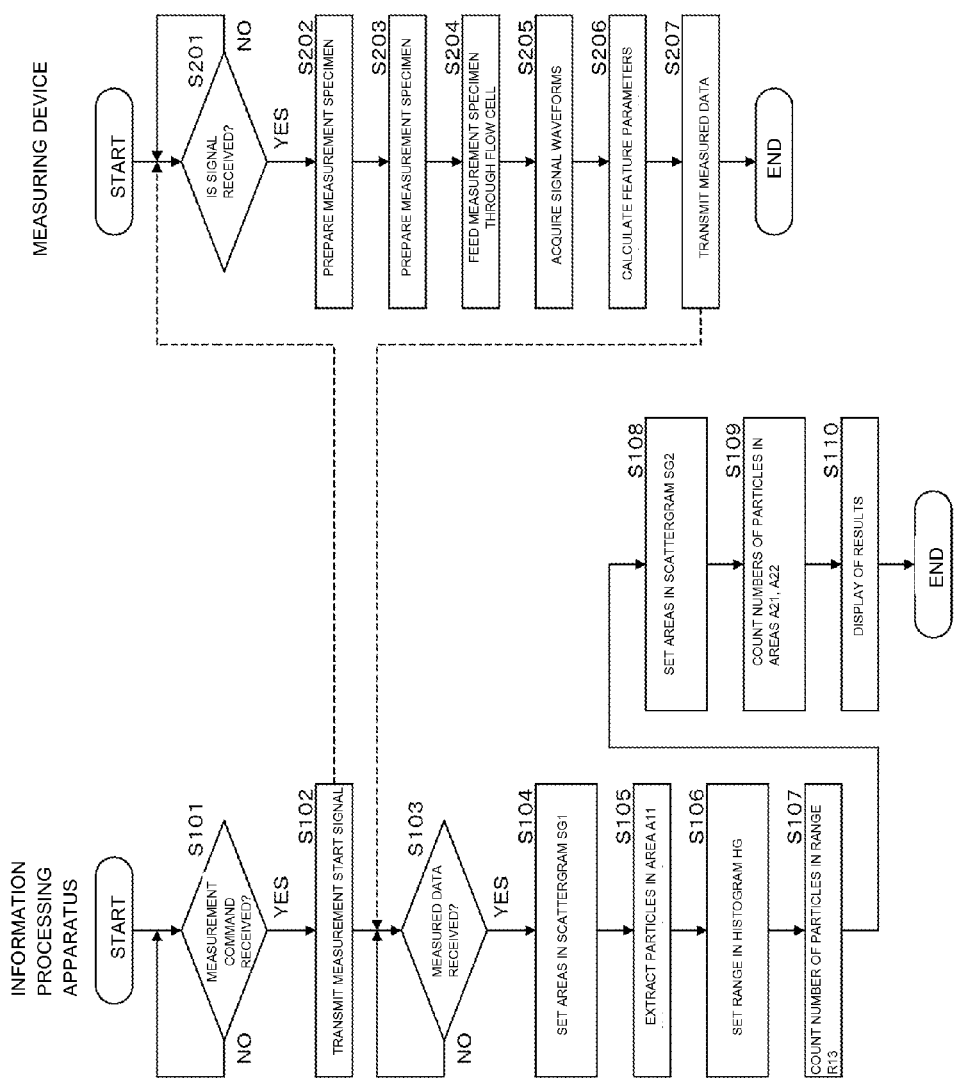
FIG. 7 is a flowchart illustrating operations performed by a measuring device and an information processing apparatus according to Operational Example 1.

FIG. 7 is a flowchart illustrating operations performed by measuring device 2 and information processing apparatus 3.

Upon receipt of a measurement command from the operator via input unit 32 (YES at S101), CPU 301 of information processing apparatus 3 transmits a measurement start signal to measuring device 2 (at S102). Meanwhile, upon receipt of the measurement start signal from information processing apparatus (YES at S201), CPU 25 of measuring device 2 prepares a measurement specimen (at S202) and feeds the prepared measurement specimen through flow cell 205 (at S203). Then, as mentioned above, the measurement specimen flowing through flow cell 205 is irradiated with laser light emitted by semiconductor laser light source 201, and, for each particle contained in the measurement specimen, forward scattered light, side scattered light and side fluorescence are detected by photodiode 209 and photomultipliers 212, 214, respectively (at S204).

Then, CPU 25 obtains signal waveforms corresponding to the detected light rays (at S205) and calculates the above-mentioned plural feature parameters based on the obtained signal waveforms (at S206). After that, CPU 25 transmits the calculated plural feature parameters (or measured data) for each particle to information processing apparatus 3 (at S207).

Meanwhile, upon receipt of the measured data (YES at S103), CPU 301 of information processing apparatus 3 sets areas A11 to A13 in scattergram SG1 (at S104). Specifically, as illustrated in FIG. 8A, the particles contained in the measured data are plotted on scattergram SG1 having as two axes a peak value (FLHP) of the side fluorescence signal and the peak value (FSCP) of the forward scattered light signal, amplified with high sensitivity by analog signal processing circuit 241. Then, areas A11 to A13 are set in scattergram SG1. Areas A11 to A13 are areas corresponding to fungi, sperm and *Trichomonas*, respectively, contained in the measurement specimen. CPU 301 extracts the particles, or the fungi, contained in area A11 on scattergram SG1 (at S105).

In FIG. 8A, FLHP of the horizontal axis reflects the degree of staining of the particles, and FSCP of the vertical axis reflects the surface area of the particles. In a case of the fungi, plural cells may be continuous as illustrated in FIG. 6A, and thus, the degree of staining and the surface area vary greatly. Thus, area A11 corresponding to the fungi is set large in the horizontal and vertical directions on scattergram SG1.

Incidentally, red blood cells are not stained by the reagent for staining a nucleic acid and are further hemolyzed, and thus, the red blood cells appear in the vicinity of the left edge on scattergram SG1 or are regarded as noise and are eliminated.

Incidentally, here, for convenience of explanation, the particles are plotted on scattergram SG1, and the particles contained in area A11 in scattergram SG1 are extracted. However, it is not necessarily required that scattergram SG1 and areas A11 to A13 be created in graphic or graphical form, and extraction of the particles contained in area A11 may be accomplished by data processing which involves extracting particles alone belonging to a specific numerical range by filtering. Likewise, it is not necessarily required that histogram HG to be described later, ranges R11 to R15 set in histogram HG, scattergrams SG2 to SG5 and areas A21 to A25 set in scattergrams SG2 to SG5 be created in graphic or graphical form, and the numbers of particles contained in ranges R11 to R15 and areas A21 to A25 may be counted by data processing.

Then, CPU 301 sets range R13 in histogram HG (at S106). Specifically, as illustrated in FIG. 8B, the particles in area A11 of FIG. 8A extracted at S105 are represented on histogram HG on which the horizontal axis indicates the width (FSCW) of the forward scattered light signal and the vertical axis indicates frequency. Then, range R13 is set in histogram HG.

In FIG. 8B, range R13 is a range corresponding to the hypha-like budding fungi contained in the measurement specimen. CPU 301 counts the particles contained in range R13 on histogram HG as the hypha-like budding fungi (at S107).

Then, CPU 301 sets areas A21, A22 in scattergram SG2 (at S108). Specifically, as illustrated in FIG. 8C, the particles in area A11 of FIG. 8A extracted at S105 are plotted on scattergram SG2 on which its two axes indicate the width (FSCW) of the forward scattered light signal and the peak value (FSCP) of the forward scattered light signal, respectively. Then, areas A21, A22 are set in scattergram SG2.

In FIG. 8C, areas A21, A22 are areas corresponding to the non-budding fungi and the process-like budding fungi, respectively (see FIG. 6B). CPU 301 counts the particles contained in areas A21, A22 on scattergram SG2 as the number of non-budding fungi and the number of process-like budding fungi, respectively (at S109).

Figure 9:
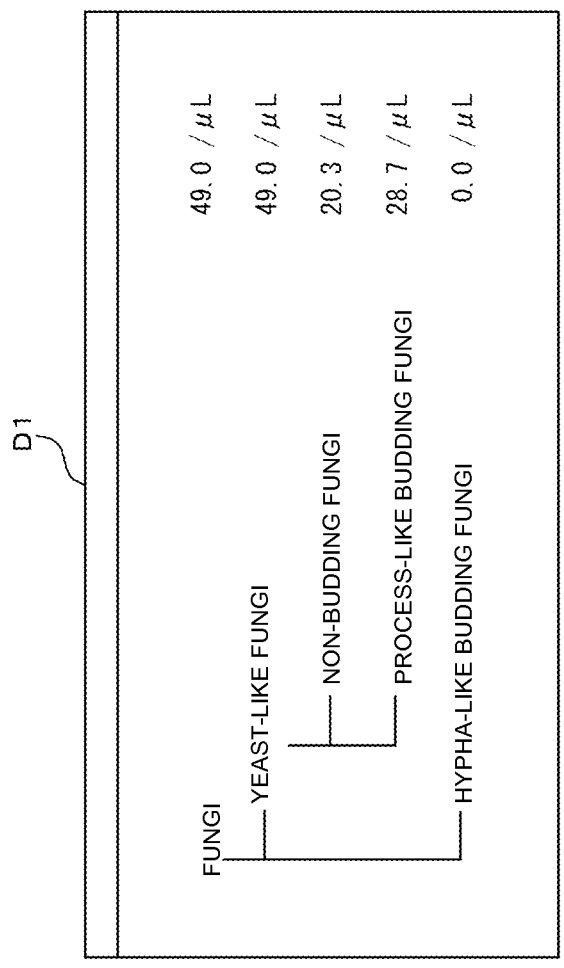
FIG. 9 is a representation illustrating a screen displayed on a display unit according to Operational Example 1.

Then, CPU 301 displays screen D1 illustrated in FIG. 9 on display unit 31, based on the numbers of particles obtained at S107 and S109 (at S110). Screen D1 displays the number of fungi, the number of yeast-like fungi, the number of non-budding fungi, the number of process-like budding fungi, and the number of hypha-like budding fungi. The number of fungi indicates a sum total of the numbers of three forms of fungi, and the number of yeast-like fungi indicates a sum total of the number of non-budding fungi and the number of process-like budding fungi. Thus, the operations performed by measuring device 2 and information processing apparatus 3 come to an end.

Operational Example 2

In Operational Example 2, fungi contained in a urine sample are classified into non-budding fungi, process-like budding fungi and hypha-like budding fungi by using FSCW and FSCP.

Figure 10A:
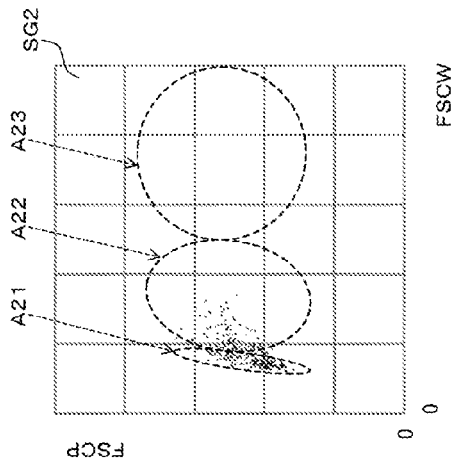
FIGS. 10A to 10D are a flowchart illustrating an operation performed by an information processing apparatus according to Operational Example 2 and a scattergram, and a flowchart illustrating an operation performed by an information processing apparatus according to Operational Example 3 and a histogram.

FIG. 10A is a flowchart illustrating an operation performed by information processing apparatus 3 in this case. In this case, S601 and S602 are added in place of S106 to S109 illustrated in FIG. 7. Description is given below only with regard to operations performed at S601 and S602.

Figure 10B:
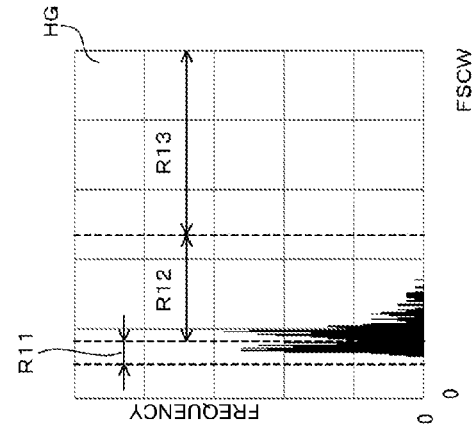

CPU 301 sets areas A21 to A23 in scattergram SG2 (at S601). Specifically, as illustrated in FIG. 10B, the particles in area A11 of FIG. 8A extracted at S105 are plotted on scattergram SG2 on which its two axes indicate the width (FSCW) of the forward scattered light signal and the peak value (FSCP) of the forward scattered light signal, respectively. Then, areas A21 to A23 are set in scattergram SG2.

In FIG. 10B, areas A21 to A23 are areas corresponding to the non-budding fungi, the process-like budding fungi, and the hypha-like budding fungi, respectively (see FIG. 6B).

CPU 301 counts the particles contained in areas A21 to A23 on scattergram SG2 as the number of non-budding fungi, the number of process-like budding fungi, and the number of hypha-like budding fungi, respectively (at S602). Then, CPU 301 displays screen D1 illustrated in FIG. 9 on display unit 31, based on the numbers of particles obtained at S202 (at S110).

Operational Example 3

In Operational Example 3, fungi contained in a urine sample are classified into non-budding fungi, process-like budding fungi and hypha-like budding fungi by using FSCW alone.

Figure 10C:
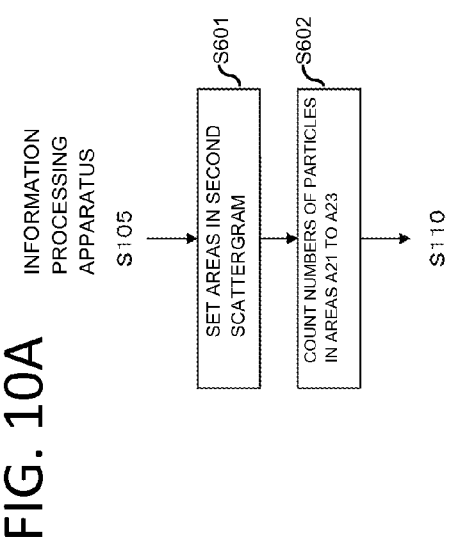

FIG. 10C is a flowchart illustrating an operation performed by information processing apparatus 3 in this case. In this case, S301 and S302 are added in place of S106 to S109 illustrated in FIG. 7. Description is given below only with regard to operations performed at S301 and S302.

Figure 10D:
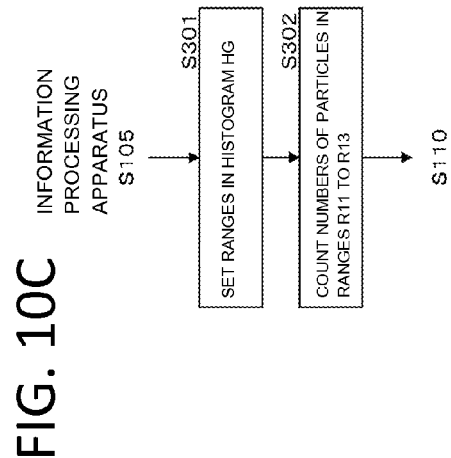

CPU 301 sets ranges R11 to R13 in histogram HG (at S301). Specifically, as illustrated in FIG. 10D, the particles in area A11 of FIG. 8A extracted at S105 are represented on histogram HG on which the horizontal axis indicates the width (FSCW) of the forward scattered light signal and the vertical axis indicates the frequency. Then, ranges R11 to R13 are set in histogram HG.

In FIG. 10D, ranges R11 to R13 are ranges corresponding to the non-budding fungi, the process-like budding fungi, and the hypha-like budding fungi, respectively. Range R13 is the same as range R13 of FIG. 8B. Ranges R11, R12 correspond to ranges of areas a1, a2, respectively, of FIG. 6B in the direction of the horizontal axis. Incidentally, the ranges of areas a1, a2 of FIG. 6B in the direction of the horizontal axis partially overlap each other, and thus, in an example of FIG. 10D, a threshold is set so as to enable a clear distinction between the non-budding fungi and the process-like budding fungi. As illustrated in FIG. 10D, the frequency in the vicinity of a boundary between ranges R11, R12 is still lower than the peak of the frequency in range R11 and the peak of the frequency in range R12.

CPU 301 counts the numbers of particles contained in ranges R11 to R13 on histogram HG as the number of non-budding fungi, the number of process-like budding fungi, and the number of hypha-like budding fungi, respectively (at S302). Then, CPU 301 displays screen D1 illustrated in FIG. 9 on display unit 31, based on the numbers of particles obtained at S302 (at S110).

Operational Example 4

In Operational Examples 1 to 3, an example is given in which fungi are classified into three groups of different forms. In Operational Example 4 given below, description is given with regard to an example in which fungi are classified into two groups of different forms, specifically, a group of budding fungi and a group of non-budding fungi.

Figure 11A:
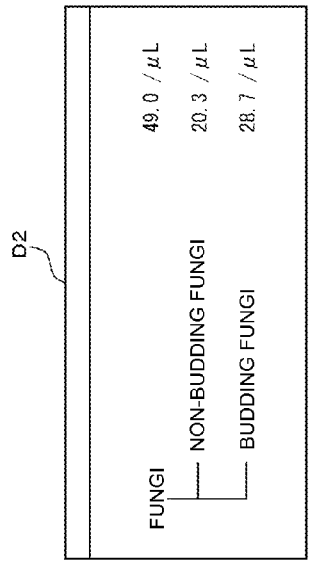
FIGS. 11A to 11D are a flowchart illustrating an operation performed by an information processing apparatus according to Operational Example 4, a histogram, a scattergram, and a representation illustrating a screen displayed on a display unit.

FIG. 11A is a flowchart illustrating an operation performed by information processing apparatus 3 in Operational Example 4. In this case, S401 and S402 are added in place of S106 to S109 illustrated in FIG. 7. Description is given below only with regard to operations performed at S401 and S402.

Figure 11C:
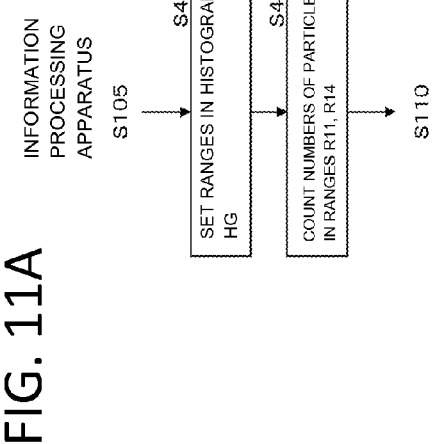
Figure 11B:
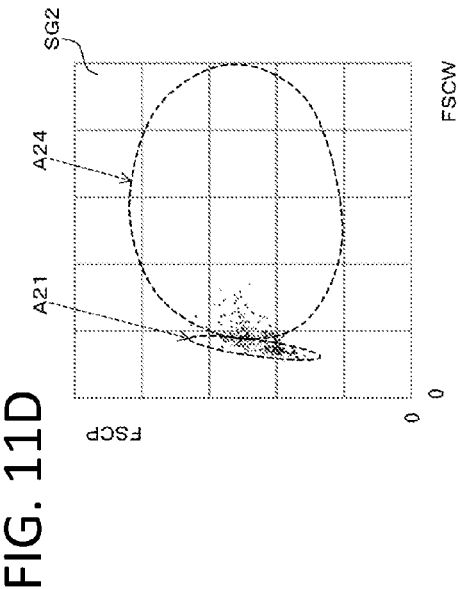

CPU 301 sets ranges R11, R14 in histogram HG (at S401). Specifically, as illustrated in FIG. 11B, the particles in area A11 of FIG. 8A extracted at S105 are represented on histogram HG on which the horizontal axis indicates the width (FSCW) of the forward scattered light signal and the vertical axis indicates the frequency. Then, ranges R11, R14 are set in histogram HG. In FIG. 11B, range R11 is the same range as range R11 of FIG. 10D, and range R14 is a range corresponding to a combination of ranges R12, R13 of FIG. 10D.

CPU 301 counts the numbers of particles contained in ranges R11, R14 on histogram HG as the number of non-budding fungi and the number of budding fungi, respectively (at S402). Then, CPU 301 displays screen D2 illustrated in FIG. 11C on display unit 31, based on the numbers of particles obtained at S402 (at S110). Screen D2 displays the number of fungi, the number of non-budding fungi, and the number of budding fungi.

Figure 11D:
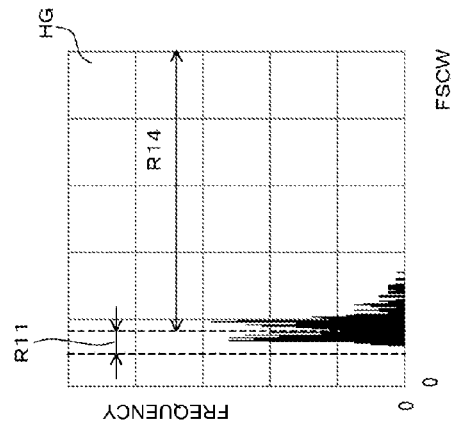

It is to be noted that, in Operational Example 4, ranges R11, R14 are set in histogram HG to discriminate between the budding fungi and the non-budding fungi, but the invention is not so limited and areas A21, A24 may be set in scattergram SG2 as illustrated in FIG. 11D to discriminate therebetween. In FIG. 11D, area A21 is the same area as area A21 of FIG. 10B, and area A24 is an area including areas A22, A23 of FIG. 10B. In this case, at S401 of FIG. 11A, areas A21, A24 are set in scattergram SG2, and, at S402, the numbers of particles contained in areas A21, A24 are counted. Then, screen D2 illustrated in FIG. 11C is displayed on display unit 31, based on counted results. Thereby, the same effect as that in a case where histogram HG illustrated in FIG. 11B is used can be achieved.

Also, the screen of FIG. 11C may include a button to subclassify the budding fungi. In this case, the operator operates the button thereby to form branches indicating "process-like budding fungi" and "hypha-like budding fungi," respectively, from the "budding fungi" on the screen and then display counted results in the branches. Counting the fungi for the branches is accomplished for example by setting areas in a scattergram or a histogram, as is the case with FIGS. 10B, 10D.

Operational Example 5

In Operational Example 4 described above, fungi are classified into budding fungi (i.e. process-like budding fungi and hypha-like budding fungi) and the other fungi (i.e. non-budding fungi). In Operational Example 5 given below, description is given with regard to an example in which fungi are classified into two groups of different forms, specifically, hypha-like budding fungi and the other fungi (i.e. yeast-like fungi).

Figure 12A:
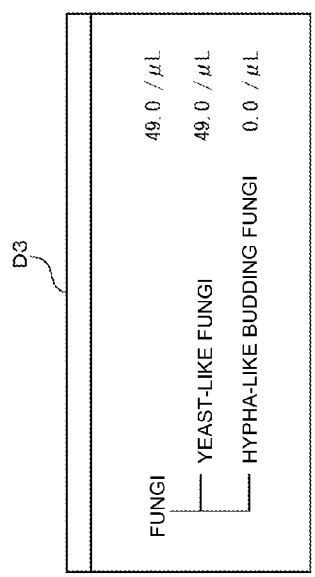
FIGS. 12A to 12D are a flowchart illustrating an operation performed by an information processing apparatus according to Operational Example 5, a histogram, a scattergram, and a representation illustrating a screen displayed on a display unit.

FIG. 12A is a flowchart illustrating an operation performed by information processing apparatus 3 in Operational Example 5. In this case, S501 and S502 are added in place of S106 to S109 illustrated in FIG. 7. Description is given below only with regard to operations performed at S501 and S502.

Figure 12C:
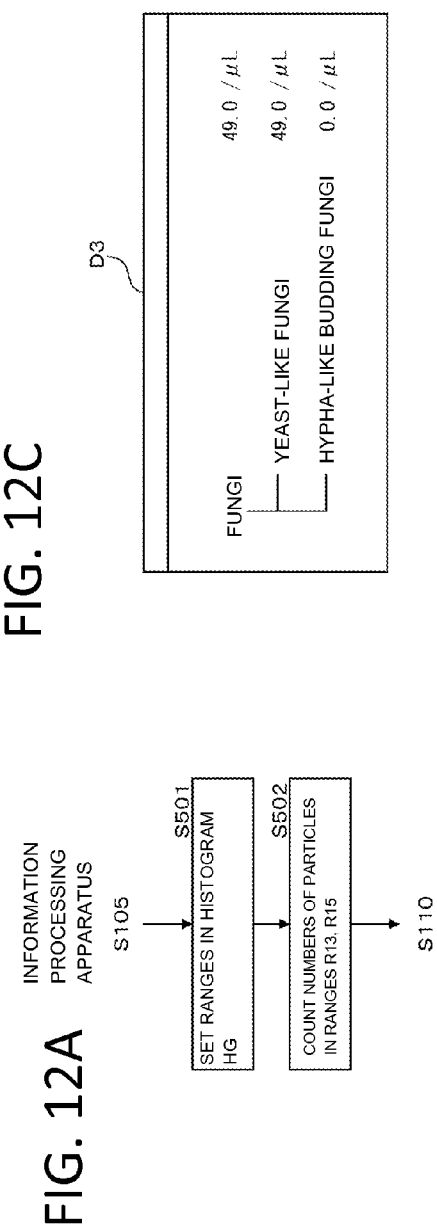
Figure 12B:
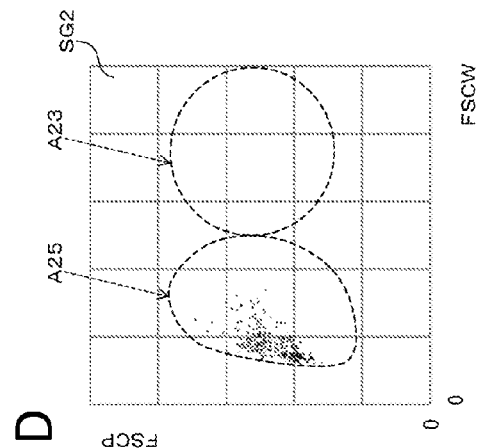

CPU 301 sets ranges R13, R15 in histogram HG (at S501). Specifically, as illustrated in FIG. 12B, the particles in area A11 of FIG. 8A extracted at S105 are represented on histogram HG on which the horizontal axis indicates the width (FSCW) of the forward scattered light signal and the vertical axis indicates the frequency. Then, ranges R13, R15 are set in histogram HG. In FIG. 12B, range R13 is the same range as range R13 of FIG. 10D, and range R15 is a range corresponding to a combination of ranges R11, R12 of FIG. 10D.

CPU 301 counts the numbers of particles contained in ranges R13, R15 on histogram HG as the number of hypha-like budding fungi and the number of yeast-like fungi, respectively (at S502). Then, CPU 301 displays screen D3 illustrated in FIG. 12C on display unit 31, based on the numbers of particles obtained at S502 (at S110). Screen D3 displays the number of fungi, the number of yeast-like fungi, and the number of hypha-like budding fungi.

Figure 12D:
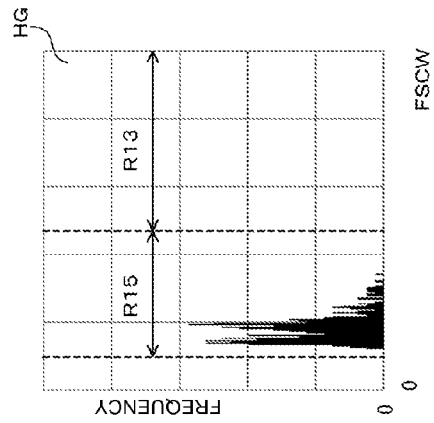

It is to be noted that, in Operational Example 5, ranges R13, R15 are set in histogram HG to discriminate between the hypha-like budding fungi and the yeast-like fungi, but the invention is not so limited and areas A23, A25 may be set in scattergram SG2 as illustrated in FIG. 12D to discriminate therebetween. In FIG. 12D, area A23 is the same area as area A23 of FIG. 10B, and area A25 is an area including areas A21, A22 of FIG. 10B. In this case, at S501 of FIG. 12A, areas A23, A25 are set in scattergram SG2, and, at S502, the numbers of particles contained in areas A23, A25 are counted. Then, screen D3 illustrated in FIG. 12C is displayed on display unit 31, based on counted results. Thereby, the same effect as that in a case where histogram HG illustrated in FIG. 12B is used can be achieved.

Although embodiments of the invention are described above, the invention is not limited to the above-described embodiments. Besides the above, various changes may also be made to embodiments of the invention.

For example, in an above-described embodiment, the width (FSCW) of the forward scattered light signal is used as the parameter reflecting the length of a fungus; however, the invention is not so limited, and other feature parameters reflecting the lengths of fungi may be used. For example, a width (SSCW) of the side scattered light signal may be used.

Figure 13A:
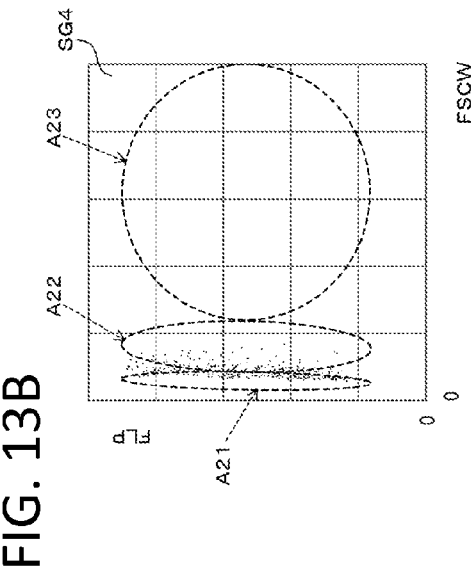
FIGS. 13A to 13C are graphs illustrating a scattergram according to Modification.
Figure 13B:
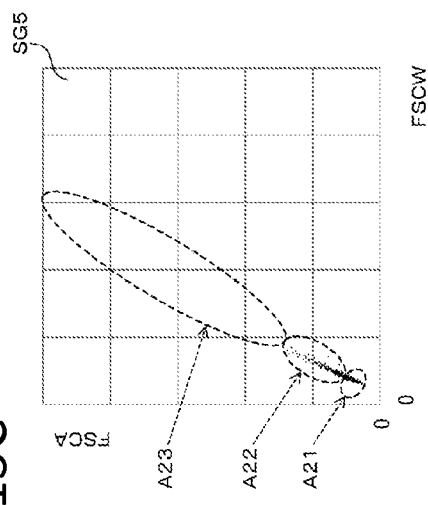
Figure 13C:
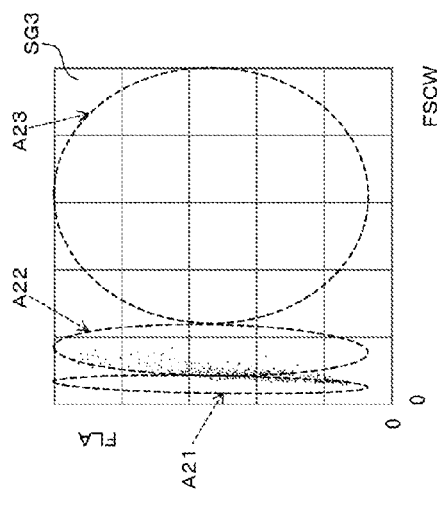

In an above-described embodiment, the peak value (FSCP) of the forward scattered light signal is used as the parameter reflecting the number of cells contained in a fungus; however, the invention is not so limited, and other feature parameters reflecting the numbers of cells contained in fungi may be used. For example, an area (FLA) of the side fluorescence signal, a peak value (FLP) of the side fluorescence signal, an area (FSCA) of the forward scattered light signal or the like may be used as other feature parameters reflecting the numbers of cells contained in fungi. Scattergram SG3 of FIG. 13A is an example of a scattergram on which the area (FLA) of the side fluorescence signal is used as the vertical axis, in place of scattergram SG2. Scattergram SG4 of FIG. 13B is an example of a scattergram on which the peak value (FLP) of the side fluorescence signal is used as the vertical axis, in place of scattergram SG2. Scattergram SG5 of FIG. 13C is an example of a scattergram on which the area (FSCA) of the forward scattered light signal is used as the vertical axis, in place of scattergram SG2. These scattergrams may also be used to classify the forms of fungi.

In Operational Examples 1, 2, 4, 5 described above, two types of parameters, specifically, the parameter (FSCW) reflecting the length of cells and the parameter (FSCP) reflecting the number of cells contained in a fungus, are used in combination to classify fungi into plural groups of different forms; however, three or more types of parameters may be used in combination. For example, three types of parameters in total, including any two of the parameters (FSCP, FLA, FLP, and FSCA) reflecting the numbers of cells contained in fungi, and the parameter (FSCW or SSCW) reflecting the length of cells, may be used to classify fungi into plural groups of different forms. In this case, a three-dimensional scattergram, rather than two-dimensional scattergrams such as are illustrated by example as SG2 to SG5, is generated, and the forms of fungi are classified based on the three-dimensional scattergram.

Also, in Operational Examples 1 to 5 described above, counted results are all displayed as results of classification of the forms of fungi; however, it is not necessarily required that the counted results be all displayed. For example, although hypha-like budding fungi may be contained in a urine sample of a serious case having significantly impaired immunity, the occurrence rate of hypha-like budding fungi is not high. Therefore, a counted result of hypha-like budding fungi may be displayed only when the counted result is equal to or more than a predetermined number. Alternatively, when the counted result of hypha-like budding fungi is equal to or more than the predetermined number, a lone flag indicating that a patient may be a serious case may be displayed without the counted result being displayed. In still another embodiment, the counted results of fungi alone may be displayed as a default, and counted results of the forms of fungi may be displayed when a user makes a request to display detailed counted results.

Figure 14B:
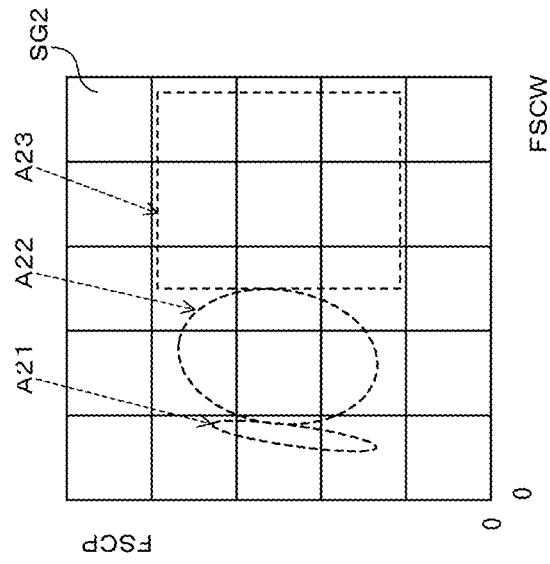
FIGS. 14A and 14B are graphs illustrating a scattergram according to Modification.
Figure 14A:
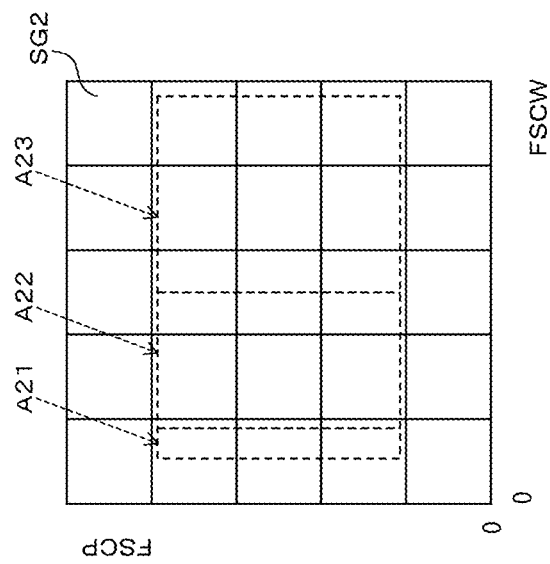

In the above-described embodiment, areas A21 to A23 set on scattergram SG2 may be set so that their adjacent boundary lines are parallel to the vertical axis as illustrated in FIG. 14A. In this case, dust or the like other than fungi, plotted above and under areas A21 to A23, can be removed. Also, areas A21 to A23 set on scattergram SG2 may be set such that each has any one of a circular shape and a rectangular shape as illustrated in FIG. 14B.

In the above-described embodiment, areas A21 to A25 are predetermined fixed areas; however, the areas are not so limited but may be fine-adjusted as appropriate, based on the fixed areas. Likewise, ranges R11 to R15 are predetermined fixed ranges; however, the ranges are not so limited but may be range adjusted as appropriate, based on the fixed ranges. Also, ranges R11 to R15 are not necessarily limited to those illustrated in the above-described embodiment but may be appropriately adjusted to ranges in which non-budding fungi, process-like budding fungi and hypha-like budding fungi can be accurately extracted.

Figure 15:
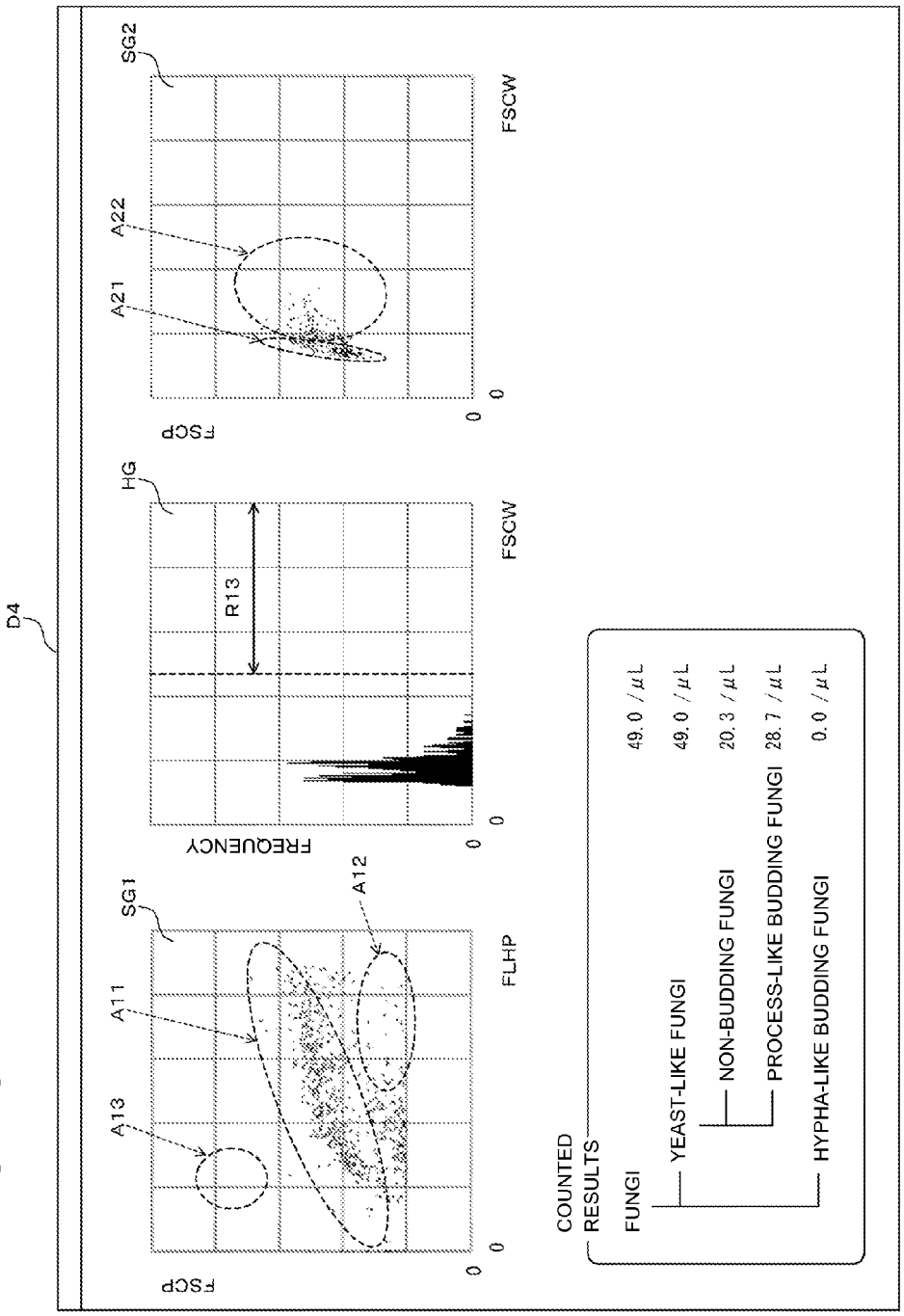
FIG. 15 is a representation illustrating a screen displayed on a display unit according to Modification.

In the above-described embodiment, the numbers of forms of fungi are displayed on display unit 31; however, the invention is not so limited, and screen D4 displaying scattergram SG1, scattergram SG2 and histogram HG together with the numbers of forms of fungi may be displayed on display unit 31. FIG. 15 illustrates screen D4 displayed in Operational Example 1. Incidentally, screen D4 displays area A11 used to extract fungi, and ranges R11 to R15 and areas A21 to A25 used to classify the forms of fungi, as appropriate. Incidentally, scattergram SG1 used to extract fungi may be omitted from screen D4.

Also, in the above-described embodiment, screens D1 to D4 displaying the numbers of forms of fungi are displayed on display unit 31; however, the invention is not so limited, and the numbers of forms of fungi may be outputted as voice by a speaker of information processing apparatus 3.

Also, in the above-described embodiment, the reagent for hemolyzing red blood cells and staining a nucleic acid is used to extract a group of fungi from area A11 of scattergram SG1 as illustrated in FIG. 8A; however, the invention is not so limited, and any method may be used to extract a group of fungi. For example, as described in Japanese Patent Application Publication No. 2006-105625, cells of fungi may be internally stained without hemolyzing red blood cells, thereby to extract a group of fungi.

Also, in the above-described embodiment, creation of scattergram SG1 and setting of areas A11 to A13, creation of scattergram SG2 and setting of areas A21 to A25, and creation of histogram HG and setting of ranges R11 to R15 are illustrated as separate steps, respectively. However, it is not necessarily required that a series of steps be executed in sequence to discriminate among the forms of fungi, and, for example, the forms of fungi may be discriminated according to whether or not plural data related to particles satisfy predetermined conditions.

For example, in Operational Example 1, if FLHP, FSCW and FSCP related to particles are included in ranges of FLHP and FSCP corresponding to area A11 illustrated in FIG. 8A and are included in range R13 illustrated in FIG. 8B, the particles may be judged as hypha-like budding fungi. Also, if FLHP, FSCW and FSCP related to particles are included in the ranges of FLHP and FSCP corresponding to area A11 illustrated in FIG. 8A and are included in ranges of FSCW and FSCP corresponding to area A21 illustrated in FIG. 8C, the particles may be judged as non-budding fungi. Also, if FLHP, FSCW and FSCP related to particles are included in the ranges of FLHP and FSCP corresponding to area A11 illustrated in FIG. 8A and are included in ranges of FSCW and FSCP corresponding to area A22 illustrated in FIG. 8C, the particles may be judged as process-like budding fungi. In this case, data related to particles are applied to a predetermined conditional expression, and, if the particles satisfy a conditional clause defined by the conditional expression, the particles are assigned to a category defined by the conditional expression. Likewise, in other Operational Examples, data related to particles are applied to a predetermined conditional expression, and, if the particles satisfy a conditional clause defined by the conditional expression, the particles are assigned to a category defined by the conditional expression.

As described above, according to embodiments, a urine sample analyzer and a urine sample analyzing method capable of classifying fungi according to the forms of fungi by flow cytometry can be provided.

Besides, various changes can be made as appropriate to the embodiment of the invention within the scope of the technical concept recited in the claims.

The invention claimed is:

1. A urine sample analyzer for analyzing particles contained in a urine sample and outputting analytical results, comprising:
a flow cell that accepts a measurement specimen, the measurement specimen comprising a urine sample mixed with a reagent;

a light irradiation unit positioned to irradiate the flowing measurement specimen with light;

a light detector that detects light from individual particles in the flowing measurement specimen; and a data processor configured to receive signal from the light detector, process the signal to obtain parameter information corresponding to a length of a cell cluster, and classify fungi in the measurement specimen into at least budding fungi and non budding fungi by using the parameter information.

2. The urine sample analyzer according to claim 1, wherein the data processor classifies the fungi into at least hypha-like budding fungi and non hypha-like budding fungi.

3. The urine sample analyzer according to claim 1, wherein the data processor uses a width of a scattered light signal from the light detector, as the parameter information corresponding to the length of the cell cluster.

4. The urine sample analyzer according to claim 1, wherein the data processor classifies the fungi by using the parameter information corresponding to the length of the cell cluster and a second parameter information corresponding to number of cells contained in the cell cluster.

5. The urine sample analyzer according to claim 4, wherein the data processor classifies the fungi into three different groups by using the parameter information corresponding to the length of the cell cluster and the second parameter information.

6. The urine sample analyzer according to claim 4, wherein the data processor uses, as the second parameter information, a peak value or an area of scattered light signal obtained by the light detector, or a peak value or an area of a fluorescence signal obtained by the light detector.

7. The urine sample analyzer according to claim 1, wherein the data processor classifies the fungi into hypha-like budding fungi, process-like budding fungi, and non-budding fungi.

8. The urine sample analyzer according to claim 1, wherein the data processor determines a group of fungi from the particles contained in the measurement specimen and classifies the determined group of fungi into subgroups having different forms, by using the parameter information obtained from the particles.

9. The urine sample analyzer according to claim 8, wherein the data processor determines the group of fungi from the particles contained in the measurement specimen, based on fluorescence signal information and scattered light signal information from the light detector.

10. A urine sample analyzer for analyzing particles contained in a urine sample and outputting analytical results, comprising:

a flow cell that accepts a measurement specimen, the measurement specimen comprising a urine sample mixed with a reagent;

a light irradiation unit positioned to irradiate the flowing measurement specimen with light;

a light detector that detects light from individual particles in the flowing measurement specimen; and a data processor configured to receive signal from the light detector, process the signal to obtain parameter information corresponding to a length of a cell cluster, and classify fungi in the measurement specimen into at least hypha-like budding fungi and non hypha-like budding fungi by using the parameter information.

11. The urine sample analyzer according to claim 10, wherein the data processor uses a width of a scattered light signal from the light detector, as the parameter information corresponding to the length of the cell cluster.

12. The urine sample analyzer according to claim 10, wherein the data processor classifies the fungi by using the parameter information corresponding to the length of the cell cluster and a second parameter information corresponding to number of cells contained in the cell cluster.

13. The urine sample analyzer according to claim 12, wherein the data processor classifies the fungi into three different groups by using the parameter information corresponding to the length of the cell cluster and the second parameter information.

14. The urine sample analyzer according to claim 12, wherein the data processor uses, as the second parameter information, a peak value or an area of scattered light signal obtained by the light detector, or a peak value or an area of a fluorescence signal obtained by the light detector.

15. The urine sample analyzer according to claim 10, wherein the data processor classifies the fungi into hypha-like budding fungi, process-like budding fungi, and non-budding fungi.

16. The urine sample analyzer according to claim 10, wherein the data processor determines a group of fungi from the particles contained in the measurement specimen and classifies the determined group of fungi into subgroups having different forms, by using the parameter information obtained from the particles.

17. The urine sample analyzer according to claim 16, wherein the data processor determines the group of fungi from the particles contained in the measurement specimen, based on fluorescence signal information and scattered light signal information from the light detector.

18. A urine sample analyzer for analyzing particles contained in a urine sample and outputting analytical results, comprising:

a flow cell that accepts a measurement specimen, the measurement specimen comprising a urine sample mixed with a reagent;

a light irradiation unit positioned to irradiate the flowing measurement specimen with light;

a light detector that detects light from individual particles in the flowing measurement specimen; and a data processor configured to receive signal from the light detector, process the signal to obtain first parameter information corresponding to a length of a cell cluster and a second parameter information corresponding to number of cells contained in the cell cluster, and classify fungi in the measurement specimen into three different groups by using the first parameter information and the second parameter information.

19. A urine sample analyzer for analyzing particles contained in a urine sample and outputting analytical results, comprising:

a flow cell that accepts a measurement specimen, the measurement specimen comprising a urine sample mixed with a reagent;

a light irradiation unit positioned to irradiate the flowing measurement specimen with light;

a light detector that detects light from individual particles in the flowing measurement specimen; and a data processor configured to receive signal from the light detector, process the signal to obtain parameter information corresponding to a length of a cell cluster, and classify fungi in the measurement specimen into hypha-like budding fungi, process-like budding fungi and non-budding fungi by using the parameter information.

* * * * *